United States Patent [19]

Ohkura et al.

[11] Patent Number: 5,532,581
[45] Date of Patent: Jul. 2, 1996

[54] CONNECTOR FOR MEASURING APPARATUS

[75] Inventors: Tadahiro Ohkura; Toshiyuki Yoshida; Mitsuru Kainuma; Kazuo Aoki, all of Yokohama, Japan

[73] Assignee: Otax Co., Ltd., Japan

[21] Appl. No.: 240,422

[22] Filed: May 10, 1994

[30] Foreign Application Priority Data

May 13, 1993 [JP] Japan .................................. 5-111754

[51] Int. Cl.⁶ .................................................. G01R 15/08
[52] U.S. Cl. ............................ 324/115; 324/157; 324/126
[58] Field of Search ..................................... 324/115, 157, 324/126; 364/571.07, 571.04

[56] References Cited

U.S. PATENT DOCUMENTS 4,621,643  11/1986  New, Jr. et al. ......................... 128/633
4,864,226   9/1989  Tachimoto et al. ...................... 324/157
4,933,631   6/1990  Eccleston ................................ 324/115
5,119,019   6/1992  George ................................... 324/115
5,250,893  10/1993  Gambill et al. ......................... 324/115

*Primary Examiner*—Kenneth A. Wieder
*Assistant Examiner*—Kourosh Cyrus Khosravi
*Attorney, Agent, or Firm*—Lorusso & Loud

[57] ABSTRACT

In a connector apparatus employed in a measuring system, a sensor is connected by releasable connector to a measuring unit to form a standard sensor connection eliminating any requirement for calibration. The connector apparatus includes a measuring circuit containing a setting line scanning program reading a plurality of setting switches in the connector set in ON/OFF states indicating the type of sensor and correction data employed by the scanning program for measurements made by the sensor.

2 Claims, 6 Drawing Sheets

CONNECTOR FOR MEASURING APPARATUS

BACKGROUND OF THE INVENTION

1. Field of the Invention

The present invention generally relates to a connector apparatus used the a measuring apparatus. More specifically, the present invention is directed to such a connector apparatus for a measuring system, capable of outputting an identification code of a sensor to a setting line scanning program by means of a plurality of setting switches contained in this connector apparatus.

2. Description of Prior Art

Figure 1:
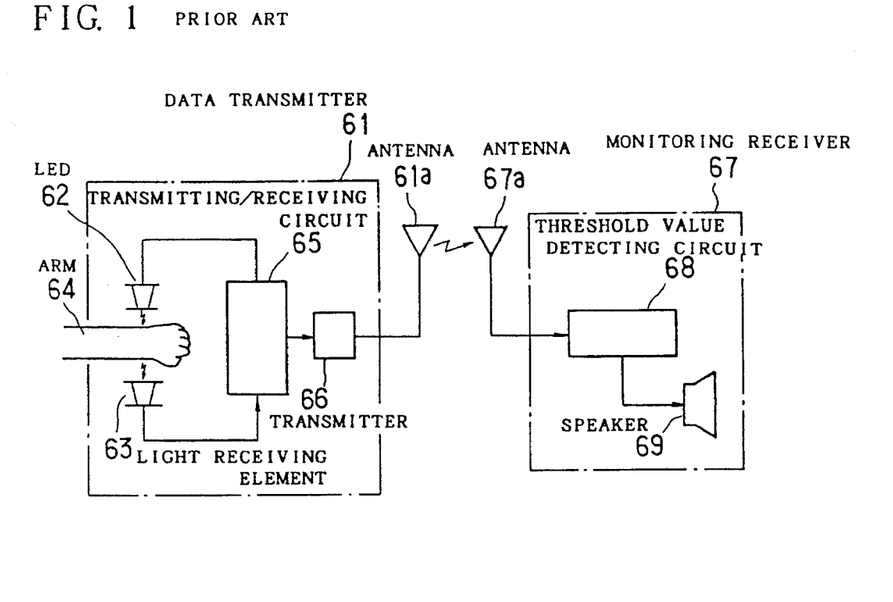
FIG. 1 schematically shows an arrangement of the conventional blood monitoring apparatus.

Conventionally, as represented in FIG. 1, a blood monitoring apparatus has been known from Japanese Patent Application No.4-33372 filed in 1992. This conventional blood monitoring apparatus includes a blood monitoring data transmitter 61 and a blood oxygen concentration monitoring receiver 67. The data transmitter 61 includes a LED 62, a light receiving element 63, an infrared transmitting/receiving circuit 65, a radio transmitter 66, and a transmitting antenna 61a. The blood oxygen concentration monitoring receiver 67 includes a receiving antenna 67a, a oxygen concentration threshold value detecting circuit 68, and a speaker 69 for broadcasting warning of a decrease in oxygen concentration.

When the infrared ray emitted from the LED 62 penetrates through the arm 64 of the human body and then impinges upon the light receiving element 63, the light receiving element 63 transmits wavelength data indicative of variations in the absorption ratio caused by the oxygen concentration in the blood to the infrared transmitting/receiving circuit 65. The wavelength data acquired by the infrared transmitting/receiving circuit 65 is transmitted from the receiving antenna 67a via the transmitting antenna 61a to the blood oxygen concentration monitoring receiver 67.

Upon detection of lowering of the oxygen concentration, the oxygen concentration lowering warning speaker 69 is operated to announce that the oxygen concentration is lowered. The decrease of oxygen concentration caused by the wavelength data is detected by the oxygen concentration threshold value detecting circuit 68 employed in the blood oxygen concentration monitoring receiver 67.

Figure 2:
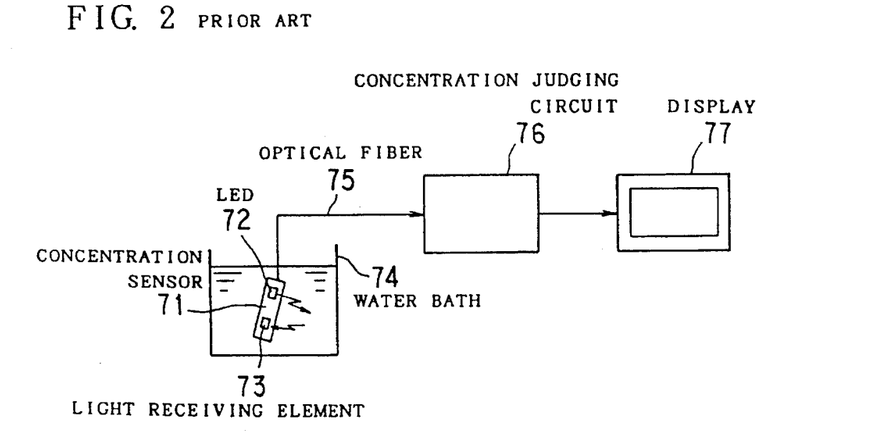
FIG. 2 is a schematic block diagram of the conventional liquid sensor.

As illustrated in FIG. 2, a liquid sensor is known from Japanese Patent Application No.4-74047 filed in 1992. This conventional sensor has a liquid concentration sensor 71 immersed in a water bath 74 and includes a LED 72 and a light receiving element 73. A liquid concentration judging circuit 76 is connected to the liquid concentration sensor 71 by the optical fiber 75 and a display 77 is connected to the circuit 76.

When the liquid concentration sensor 71 is dipped into the water bath 74 and light is irradiated from the LED 72 into the liquid contained in the water bath 74, the light propagated through this liquid is received by the light receiving element 73. Since the strengths, or intensity of the light received by the light receiving element 73 is directly proportional to the concentration of the liquid, this intensity data is processed in the liquid concentration judging circuit 76, and the processed data is displayed on the display 77.

In this case, when data is produced that a light having a specific wavelength is blocked, or passes through the liquid due to variations in the composition of this liquid, chemical changes of the liquid can be detected.

In general, an optical sensor constructed of either a pair of light emitting element/light receiving element, or only a light receiving element is manufactured in accordance with a desired measurement, and is commercially available.

In such an optical sensor and a measuring apparatus, the optical sensor is designed for a specified measurement, for instance, oxygen concentration in blood, respiration periods, pulse rates, or chemical changes in a specific fluid. The measuring apparatus is exclusively used with such a chemical sensor having the specific measuring properties.

Since there is no standard method of connecting optical sensors with measuring apparatus, a difficult manual connection sequence is performed every time an optical sensor is connected to a measuring apparatus.

Further, calibration is required in correspondence with the measurements to be performed by the measuring apparatus. Other problems include deterioration of measuring precision due to errors in calibration, and correction values must be modified in accordance with the measurements.

SUMMARY OF THE INVENTION

The present invention has been made in an attempt to solve the above-described conventional problems, and therefore has an object to provide a connector apparatus used in a measuring apparatus, in which a connection method for connection a sensor to the measuring apparatus is standardized.

Another object of the present invention is to provide a connector apparatus utilized with a measuring apparatus capable of performing a plurality of measurements, in which no calibration is required for these measurements, higher measuring precision is achieved, and a correction value is readily modified.

To achieve these objects, a connector apparatus used in a measuring apparatus according to the present invention includes a measuring unit containing a setting line scanning program; a connector including a plurality of setting switches set in ON/OFF states indicating one of a plurality of measurements for being scanned by the setting line scanning program; and a sensor connected to the connector for sensing the one indicated measurement.

In the above-described connector apparatus used to the measuring apparatus, a ROM (read-only memory) from which the measurement items are readable in accordance with the setting line scanning program, is a PROM (programmable read-only memory).

In the measuring unit, a jack is provided which is engaged with the connector.

A sensor pulse transmitting circuit for transmitting a sensor pulse via the jack engaged with the connector to the sensor is employed in the measuring apparatus.

A background noise eliminating circuit for eliminating background noise related to the sensor, which is inputted via the jack, is provided with the measuring circuit.

A sensing data shaping circuit for shaping sensing data outputted from the background noise is provided in the measuring apparatus.

In the measuring apparatus, there is provided a correction table "TBL" used in accordance with the setting line scanning program.

The correction table "TBL" is stored into an EEPROM (electrically erasable PROM).

A correction calculation program is provided with the measuring apparatus, by which the data read out from the sensor in accordance with the setting line scanning program is corrected.

A corrected data outputting circuit for outputting the corrected data which has been corrected in accordance with the correction calculation program, is employed in the measuring apparatus.

A display for representing the corrected data derived from the corrected data output circuit is provided with the measuring apparatus.

In the above-described connector apparatus used in the measuring apparatus, the ON/OFF states of the plural setting switches built in the connector are scanned in accordance with the setting line scanning program stored in the measuring apparatus. Since the connector is directly connected with the sensor, the ON/OFF states of these plural setting switches correspond with the measurement to be performed by the sensor. Thus both the type of sensor and the measurements performed thereby can be discriminated by the setting line scanning program.

The measurements to be performed are read out of the ROM in accordance with the setting line scanning program.

The connector is engaged with the jack provided on the measuring unit.

From the sensor pulse transmitting circuit provided in the measuring unit, the sensor pulse is sent out via the jack to the sensor.

The background noise in the signal input via the jack of the measuring apparatus, is eliminated by the background noise eliminating circuit.

The sensing data output from the background noise eliminating circuit is shaped by the sensing data shaping circuit.

The correction table employed in the measuring apparatus is read in accordance with the setting line scanning program.

This correction table is stored into the EEPROM.

The data corrected in accordance with the correction calculation program is output from the corrected data output circuit employed in the measuring apparatus.

Furthermore, the data corrected in the corrected data output circuit is displayed on the display provided with the measuring apparatus.

BRIEF DESCRIPTION OF THE DRAWING

For a better understanding of the present invention, reference is made of the detailed description to be read in conjunction with the accompanying drawings, in which.

DETAILED DESCRIPTION OF PREFERRED EMBODIMENTS

Referring now to drawings, a connector apparatus used in a measuring apparatus according to a preferred embodiment of the present invention will be described in detail.

Figure 3:
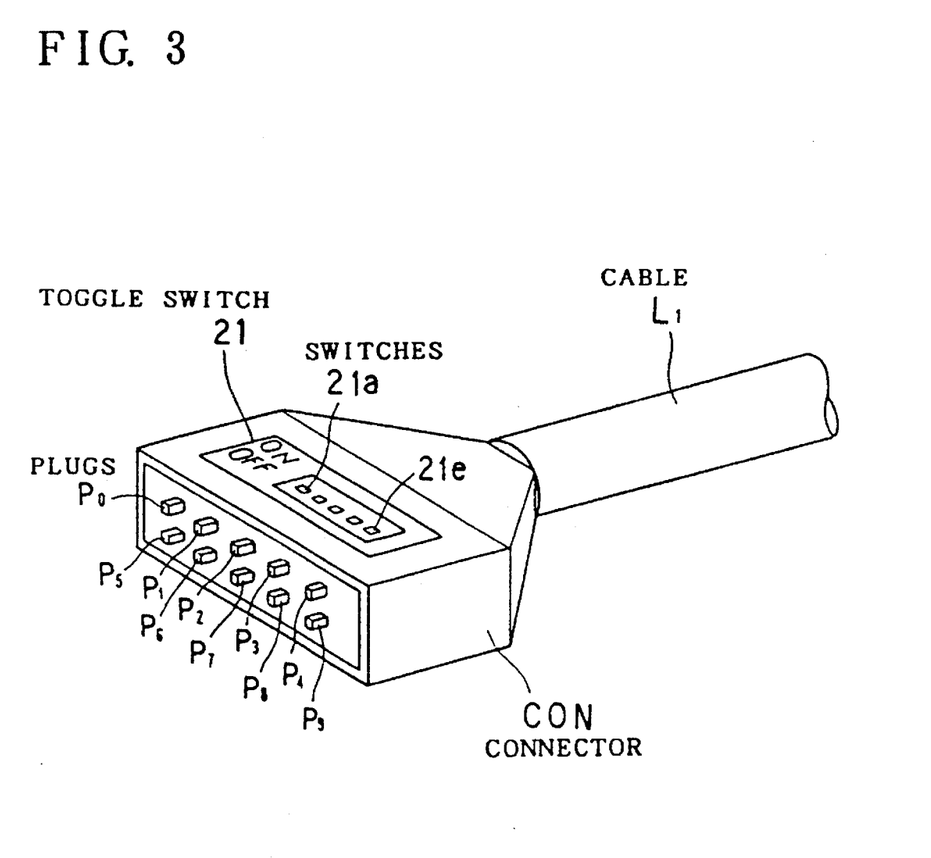
FIG. 3 is a perspective view of a connector apparatus used to a measuring apparatus, according to a preferred embodiment of the present invention.
Figure 4:
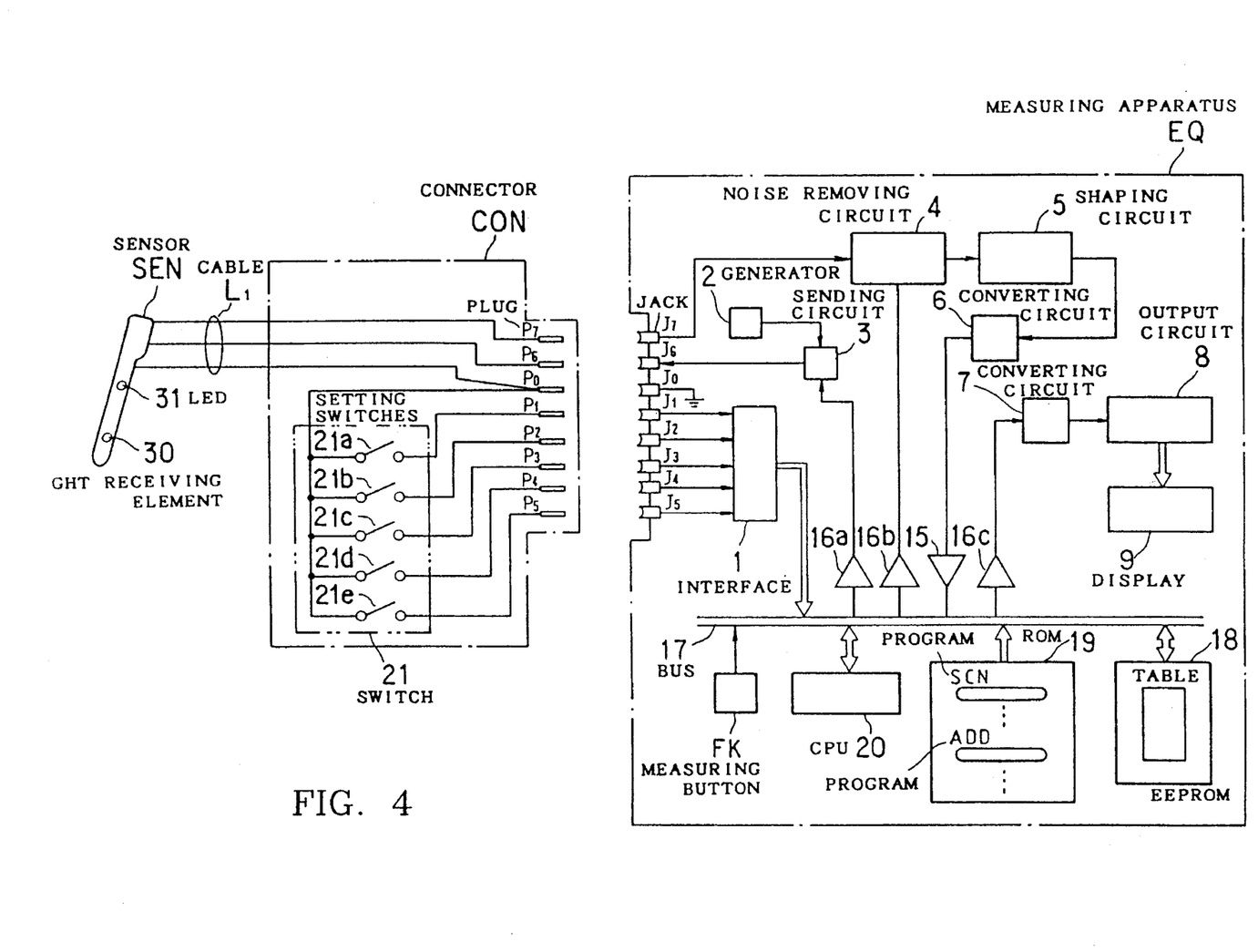
FIG. 4 is a schematic block diagram indicating the connector apparatus used in the measuring apparatus, according to a preferred embodiment of the present invention.

FIG. 3 and FIG. 4 represent a connector apparatus used in a measuring apparatus according to a preferred embodiment of the present invention. This connector apparatus includes a measuring unit or apparatus "EQ" having a stored setting line scanning program "SCN", a connector "CON" containing a plurality of setting switches $21a$ to $21e$, and a sensor "SEN" connected to this connector for performing one of a plurality of possible measurements. One of these measurements is set by way of ON/OFF states of these setting switches, which are scanned in accordance with the setting line scanning program stored in the measuring apparatus EQ.

As represented in FIG. 3, the connector CON contains an item setting toggle switch 21, and toggles of the setting switches $21a$ to $21e$ are operable on an upper surface of this connector CON. A connector/sensor cable "L1" is provided on one side of the connector CON, and plugs "P0" to "P9" (note plugs P8 and P9 are spare plugs) are provided on the other side of this connector CON.

As shown in FIG. 4, the plugs P0 to P7 of the connector CON have such a structure that these plugs can be plugged with jacks J0 to J7 employed in the measuring apparatus EQ. A sensor "SEN" employing an LED 31 and a light receiving element 30 is connected to the connector/sensor cable L1.

An item setting toggle switch 21 constructed of setting switches $21a$ to $21e$ having normally-open contacts is provided with the connector CON. One ends of these setting switches $21a$ to $21e$ are connected to the plugs P1, P2, P3, P4, P5 of the connector CON, and other ends thereof are commonly connected to the plug P0.

When the plugs P1, P2, P3, P4, P0, P5, P6 of the connector CON are plugged to the jacks J1, J2, J3, J4, J0, J5, J6 of the measuring apparatus EQ, a preparation for the measurement operation is accomplished.

As indicated by FIG. 4, the measuring apparatus EQ includes by a setting line interface 1 to which the above-explained jacks J1, J2, J3, J4, J5 have been connected, a sensor pulse sending circuit 3 to which a sensor pulse generator 2 has been connected, and a background noise removing circuit 4 constructed of an operational amplifier whose amplification is controllable. This measuring apparatus EQ further includes a sensing data shaping circuit 5, an A/D (analog-to-digital) concerting circuit 6, a D/A (digital-to-analog) converting circuit 7, a corrected data output circuit 8, and a display 9. Also, the measuring circuit EQ further contains a measuring button FK, a CPU (central processing unit) 20 having calculation registers R1 to R4, a ROM (read-only memory) 19 for storing therein a setting line scanning program SCN and a correction calculation program ADD, and an EEPROM (electrically erasable programmable ROM) 18 with a correction table TBL.

The setting line interface 1 connected with the jacks J1, J2, J3, J4, J5, is coupled to a data bus 17, and the jack J0 is coupled to a reference potential point.

The output terminal of the background noise removing circuit 4 to which the jack J7 is connected, is coupled via the sensing data shaping circuit 5, the A/D converting circuit 6, and the cable receiver 15 to the above-described data bus 17. Furthermore, cable drivers 16a, 16b, 16c connected to this data bus 17 are connected to the sensor pulse sending circuit 3, the background noise removing circuit 4, and the control input terminal of the D/A converting circuit 7.

The output terminal of the D/A converting circuit 7 is connected via the corrected data output circuit 8 to the display 9. Also, to the data bus 17, the measuring button FK, the CPU 20, the ROM 19, and the EEPROM 18 are connected.

Figure 5:
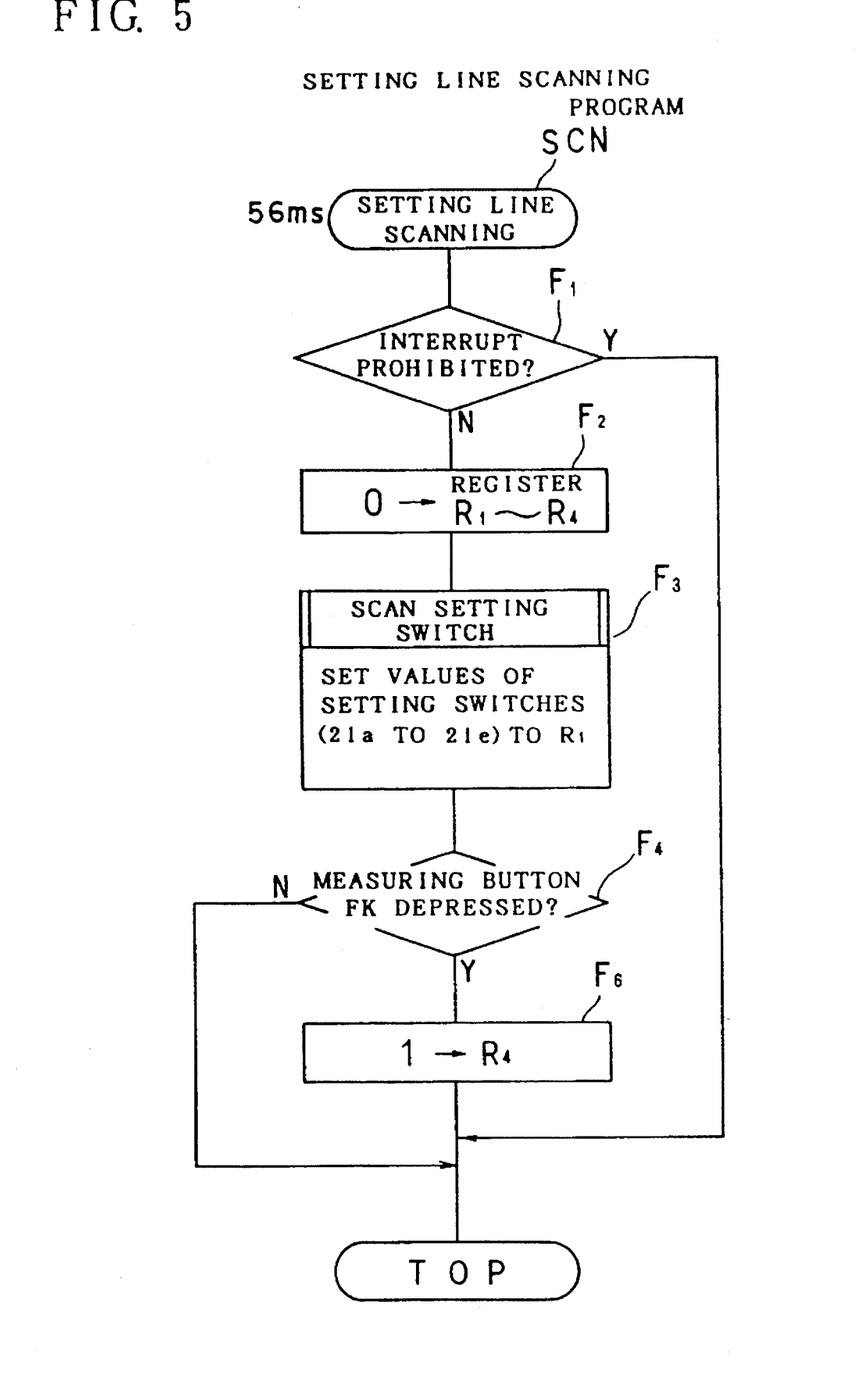
FIG. 5 is a flow chart of a setting line scanning program executed in the connector apparatus of the present invention.

The setting line scanning grogram SCN is a periodric (cyclic) program initiated by an execution managing program in a period of 56 mS (milliseconds), as indicated in FIG. 5. This program is mainly constructed of judging boxes F1, F4, processing boxes F2, F6, and a subroutine F3. At the judging box F1, a judgment is made as to whether or not an interrupt is prohibited. When it is judged that the interrupt is not prohibited at the judging box F1, the contents of the calculation registers R1 to R4 are initialized at the processing box F2.

Subsequently, the numeral values of the setting switches 2a to 2d are stored into the calculation register R1 at the setting switch scanning subroutine F3. When the measuring button FK shown in FIG. 4 is depressed, the process operation is advanced from the judging box F4 to the processing box F6. Then, after the content of the calculation register R4 is set to 1 at the processing box F6, the control operation is transferred to the execution managing program.

To the contrary, when it is so judged that the interrupt is prohibited at the previous judging box F1, and also when the judging result at the judging box F4 becomes "NO", no process operation is executed and the control operation is transferred to the execution managing program.

Figure 6:
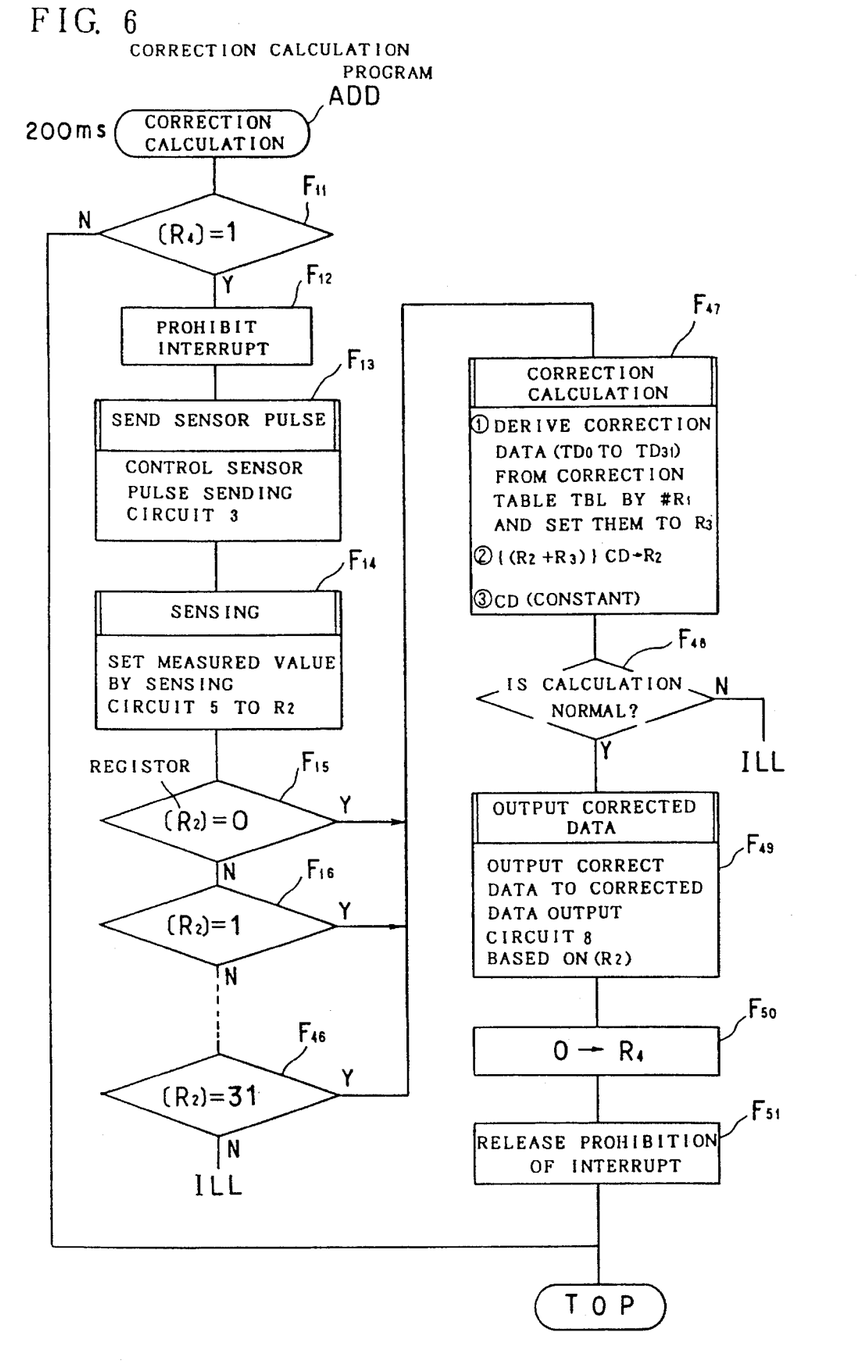
FIG. 6 is a flow chart of a correction calculation program executed in the connector apparatus of the present invention.

The correction calculation program ADD corresponds to a periodic program initiated by the execution managing program in a period of 200 mS as shown in FIG. 6. This correction calculation program is mainly arranged by judging boxes F11, F15 to F46, processing boxes F12, F50, F51, and subroutines F13, F14, F47, F49. At the first judging box F11, a judgment is made as to whether or not the content of the calculation register R4 is equal to 1. When it is so judged that the content of the calculation register R4 is 1, the interrupt is prohibited at the processing box F12, and this flow operation is advanced to the sensor pulse sending subroutine F13. In the sensor pulse sending subroutine F13, the sensor pulse sending circuit 3 represented in FIG. 4 is controlled. The measured value by the sensing circuit 5 (abbreviated from a "sensing data shaping circuit 5") is stored into the calculation register R2 at the sensing subroutine F14.

While the sensing data subroutine F14 is executed, if the numeral values of the calculation register R2 are 0 to 31, then the flow operation is advanced to the correction calculation subroutine F47. If the numeral values of this calculation register R2 are any values greater then 32, then the flow operation is advanced via the judging box F46 to an illegal function ILL, at which a warning sound is produced to announce that the measurement cannot be executed. In the correction calculation subroutine F47, a correction table TBL is referred as represented in FIG. 4.

Figure 7:
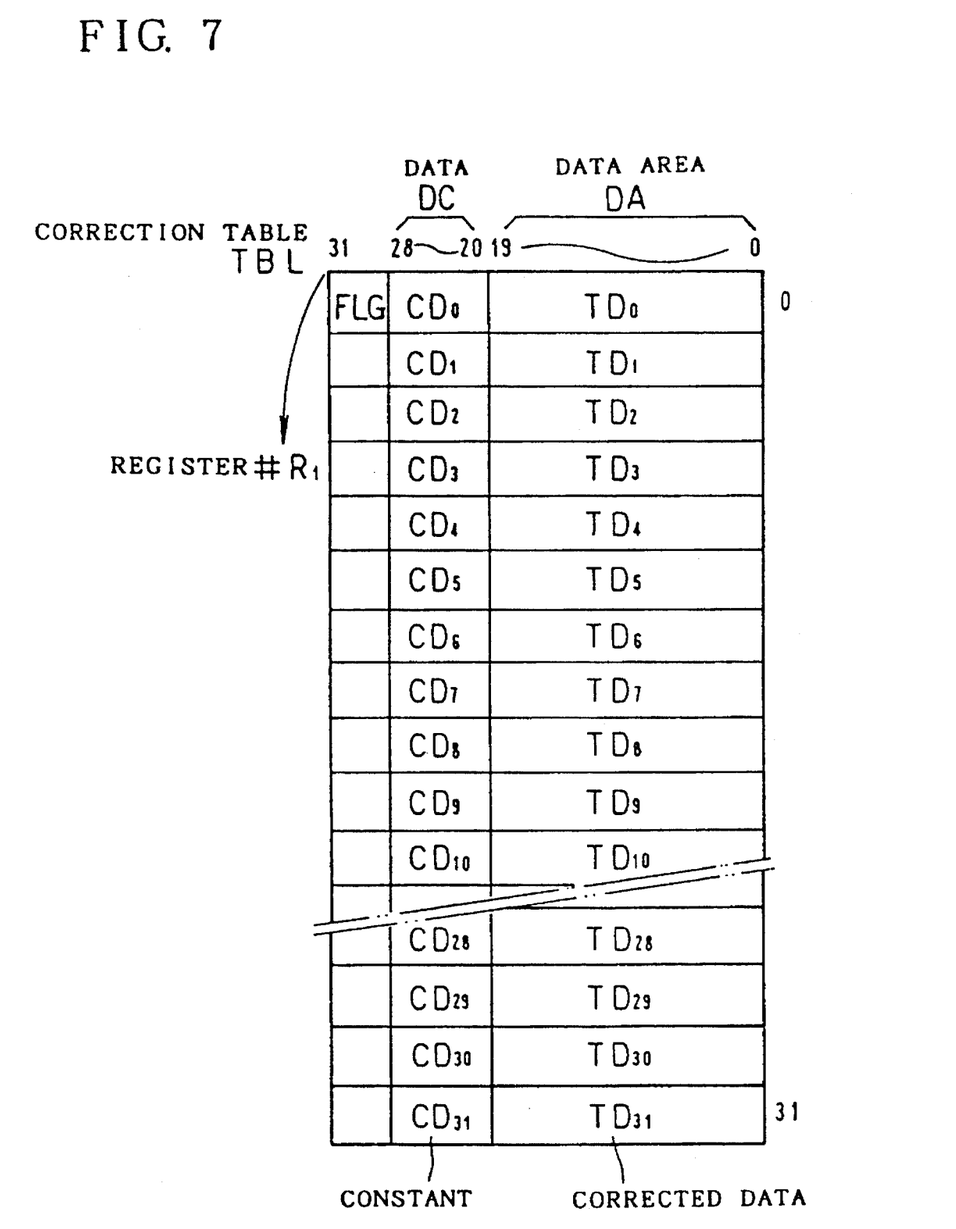
FIG. 7 schematically illustrates contents of a correction table employed in the connector apparatus of the present invention.

The correction table TBL is constructed of such a rewritable memory as the EEPROM 18 shown in FIG. 7, and owns a memory capacity of 0 to 31 words (1 word corresponding to 1 to 31 bits). The corrected data TD0 to TD31 stored in the respective data areas DA (0 to 19 bits) may be derived, or read out based upon the numeral values stored in the calculation register R1. It should be noted that bits 28 to 31 are utilized as a flag FLG, and are activated, depending upon such a condition whether or not the corrected data TD0 to TD31 are present. Constants CD0 to CD31 are stored in constant data DC (bits 20 to 27).

At (1) of the correction calculation subroutine F47, the corrected data (TD0 to TD31) read out from the correction table TBL in response to the numeral values of the calculation register R1 are stored into the calculation register R3. At (2) of the correction calculation subroutine F47, the numeral values (measured values) of the calculation register R2 are added to the numeral values (corrected data TD0 to TD31) of the calculation register R3, the added values may be multiplied by the constants CD0 to CD31, if required, and then the calculated values are stored in the calculation register R2. Next, a judgment is made as to whether or not the calculated value is normal at the judging box F48. If the calculated value is abnormal, then the process operation becomes the illegal function ILL, and then a warning sound for announcing that the measurement cannot be performed is produced. To the contrary, if the calculated value is normal, then the corrected data output subroutine F49 is executed in which the corrected data output circuit 8 is controlled in accordance with the numeral values of the calculation register R2, and the control operation is transferred to the execution managing program.

In the connector apparatus used to the measuring apparatus having such a structure, when the plugs P1, P2, P3, P4, P1, P5, P6 of the connector CON are plugged to the jacks J1, J2, J3, J4, J0, J5, J6 of the measuring apparatus EQ, the reference potential point connected to the jack J0 is connected to the plug P0 of the connector CON.

When the measuring button FK of the measuring apparatus EQ is depressed, the flow operation is advanced from the judging box F4 to the processing box F6 of the setting line scanning program SCN indicated in FIG. 5. At this processing box F6, after the content of the calculation register R4 is set to 1, the control operation is transferred to the execution calculation program.

When a judgment is made that the content of the calculation register R1 is equal to 1 at the judging box F11 of the initiated correction calculation program ADD, the interrupt is prohibited at the processing box F12. Also, the sensor pulse sending subroutine F13 and the sensing subroutine F14 are executed, so that the measured values are stored into the calculation register R2.

For instance, when only the setting switch 21a among the plural setting switches 21a to 21e of the connector CON is turned ON, since the jack J1 becomes 1 and other jacks J2, J3, J4, J5 become 0, the measurement item "1" is inputted via the setting line interface 1 into the CPU20. This measurement item 1 is stored into the calculation register R1.

When the corrected data table TBL shown in FIG. 7 is retrieved under such a condition that the numeral value stored in the calculation register R1 is used as the address, the corrected data TD1 can be read out.

Assuming now that the measurement item is wavelength data, the corrected data TD1 becomes 0.190 mV. As to the wavelength data of the light receiving element, which has been actually measured, assuming now that 860 nm is recognized as the reference value and absorbance of this reference value is 98% (0.200 mV), the wavelength data of 660 nm will be 659 nm, namely be shifted by 1 nm due to a change in absorbance caused by oxygen concentration in blood to be measured. As a result, the calculated value in this case becomes 97.5% of 659 nm (0.190 mV).

It should be noted that depending upon the measurement item, the numeral values (measured value) of the calculation register R2 are added to the numeral values (corrected data TD0 to TD63) of the calculation register R3 in (2) of the correction calculation subroutine F47, and then the added values are multiplied by the constants CD0 to CD63 defined in (3) of the correction calculation subroutine F47, and thereafter the calculated values are stored in the calculation register R2.

Furthermore, with respect to such optical data as respiration periods and pulse rates, which are not the wavelength elements, an operating sequence for previously removing fluctuation in the characteristics of the light emitting element 31 and the light receiving element 30 by the background noise removing circuit 4 under control of the CPU 20, is executed by the correction calculation program.

The sensing subroutine F14 of the correction calculation program ADD is executed, and the sensing pulse is sent out from the sensor pulse sending circuit 3 via the jack J6 to the sensor SEN.

When the sensing pulse is transmitted to the sensor SEN, the sensing data is inputted from the jack J8 to the background noise removing circuit 4.

The sensing subroutine F14 of the correction calculation program ADD is executed, the sensing data shaping circuit 5 is operated, the sensing data is converted into the digital sensing data by the A/D converting circuit 6, and finally the digital sensing data is supplied via the cable receiver 15 and the data bus 17 to the CPU 20.

The CPU 20 furnishes the inputted sending data via the D/A converting circuit 7 and the correction data output circuit 8 to the display 9 so as to display thereon the content of this sensing data.

It should be understood that this control is performed by the correction calculation program ADD.

Since the item setting toggle switch 21 constructed of the setting switches 21a to 21e capable of reading the measurement item in the setting line scanning program SCN, is provided on the connector CON, the measurement items may be freely set.

As the jacks J0 to J7 engaged with the connector CON are employed in the measuring apparatus EQ, the connection between the connector CON and the jacks J0 to J7 may be standardized.

Because the sensor pulse is sent out from the sensor pulse sending circuit 3 employed in the measuring apparatus EQ via the jack J8 engaged with the connector CON, the sensor is periodically operated thereby to assure statical reliability of the sensing data.

As the background noise is removed by the background noise removing circuit 4 employed in the measuring apparatus EQ, the sensing data are not disturbed by the background noise. As a consequence, no calibration is required.

As the sensing data outputted from the background noise removing circuit 4 is shaped by the sensing data shaping circuit 5 provided in the measuring apparatus, an error contained in the sensing data to be processed by the CPU 20 can be reduced.

Since the correction data TBL used in the setting line scanning program SCN is provided with the measuring apparatus EQ, a large number of measurement items can be selected.

Also, since this correction table TBL is employed in the EEFROM 18, the correction values may be easily modified.

The high measuring precision can be achieved since the data read by the setting line scanning program SCN is corrected by the correction calculation program employed in the measuring apparatus.

The corrected data which have been corrected by the correction calculation program ADD can be outputted from the corrected data output circuit 8 employed in the measuring apparatus EQ.

The, display 9 employed in the measuring apparatus EQ represents the content of the corrected data, and further such a fact that no measurement could be carried out, if necessary.

It should also be noted that the quantity of the setting switches 21a to 21e provided with the item setting toggle switch 21 of the connector CON in the above-described preferred embodiment is not limited to six, but may be freely selected.

As apparent from the foregoing descriptions, in accordance with the connector apparatus used to the measuring apparatus of the present invention, the method for connecting the sensor with the measuring apparatus can be standardized. Moreover, in the measuring apparatus capable of measuring a plurality of measurement items, according to the present invention, no calibration is required for the measurement items, and the high measuring precision can be realized with easily changing the correction values.

What is claimed is:

1. A connector apparatus for use in a measuring apparatus comprising:

a measuring unit containing a stored setting line scanning program, a connector containing a plurality of setting switches set in ON/OFF states indicating one of a plurality of measurements and which are scanned by the setting line scanning program, a sensor connected to the connector for performing the indicated measurement, jacks in the measuring unit for being releasably engaged with the connector, a sensor pulse transmitting circuit in the measuring unit for transmitting a sensor pulse via the jacks and the connector to the sensor, a background noise eliminating circuit in the measuring unit for eliminating background noise in a signal input from the sensor via the jacks, a sensing data shaping circuit in the measuring unit for shaping sensing data output from the background noise eliminating circuit, a correction table in the measuring unit used in accordance with the setting line scanning program, a correction calculation program in the measuring unit for correcting data read out from the sensor in accordance with the setting line scanning program, and a corrected data outputting circuit in the measuring unit for outputting the corrected data which has been corrected in accordance with the correction calculation program.

2. A connector apparatus as claimed in claim 1 wherein the correction calculation program corrects data using correction data from the correction table selected in correspondence with the setting of the setting switches.

\* \* \* \* \*

UNITED STATES PATENT AND TRADEMARK OFFICE
CERTIFICATE OF CORRECTION

PATENT NO. : 5,532,581
DATED : July 2, 1996
INVENTOR(S) : OHKURA et al

It is certified that error appears in the above-indentified patent and that said Letters Patent is hereby corrected as shown below:

Col. 1, line 9, delete "the" insert --in--;
      line 25, delete "a", second instance, insert --an--;
      line 46, delete "liquid";
      line 59, "strengths" should read --strength--.

Col. 2, line 15, "Further," should read --Furthermore,--.

Col. 5, line 8, "grogram" should read --program--.

Col. 8, line 9, "The," should read --The--.

Signed and Sealed this

Seventh Day of January, 1997

Attest:

BRUCE LEHMAN

*Attesting Officer*     *Commissioner of Patents and Trademarks*